(12) United States Patent
Wang

(10) Patent No.: US 8,386,001 B2
(45) Date of Patent: Feb. 26, 2013

(54) ROCKER-CHUTE TYPE FINGER-CLIPPED OXIMETER

(75) Inventor: Weihu Wang, Beijing (CN)

(73) Assignee: Beijing Choice Electronic Technology Co., Ltd., Beijing (CN)

( * ) Notice: Subject to any disclaimer, the term of this patent is extended or adjusted under 35 U.S.C. 154(b) by 391 days.

(21) Appl. No.: 12/866,405

(22) PCT Filed: May 8, 2008

(86) PCT No.: PCT/CN2008/070911
§ 371 (c)(1),
(2), (4) Date: Aug. 5, 2010

(87) PCT Pub. No.: WO2009/135357
PCT Pub. Date: Nov. 12, 2009

(65) Prior Publication Data
US 2010/0317944 A1    Dec. 16, 2010

(51) Int. Cl.
*A61B 5/00* (2006.01)
(52) U.S. Cl. ...................................................... 600/323
(58) Field of Classification Search .................. 600/323
See application file for complete search history.

(56) References Cited

U.S. PATENT DOCUMENTS

| 5,490,523 | A | * | 2/1996 | Isaacson et al. | ............... 600/323 |
| 6,154,667 | A | | 11/2000 | Miura et al. | |
| 6,615,064 | B1 | | 9/2003 | Aldrich | |
| 6,643,531 | B1 | * | 11/2003 | Katarow | ........................ 600/344 |
| 7,254,434 | B2 | * | 8/2007 | Schulz et al. | .................. 600/344 |
| 2003/0045784 | A1 | | 3/2003 | Palatnik et al. | |
| 2009/0043180 | A1 | * | 2/2009 | Tschautscher et al. | ....... 600/323 |

FOREIGN PATENT DOCUMENTS

| CN | 1578640 A | 2/2005 |
| JP | 2088040 A | 3/1990 |
| JP | 2088042 A | 3/1990 |
| JP | 6125882 A | 5/1994 |

* cited by examiner

*Primary Examiner* — Clayton E Laballe
*Assistant Examiner* — Dennis Hancock
(74) *Attorney, Agent, or Firm* — The Webb Law Firm

(57) ABSTRACT

The present invention discloses a finger-clipped oximeter comprising an upper case (2) and a lower case (1), wherein one of the upper case (2) and the lower case (1) is provided with a guide post (12) which enables the upper case (2) and the lower case (1) to depart from and approach to each other vertically, the other of the upper case (2) and the lower case (1) is provided with a guide sleeve (13) which enables the upper case (2) and the lower case (1) to depart from and approach to each other vertically, and a return spring (9) is provided between an end of the guide post (12) and the case provided with the guide sleeve (13). One of the upper case (2) and the lower case (1) is provided with rockers (7, 8) which are used to facilitate the upper case (2) and the lower case (1) to depart from and approach to each other vertically, the other of the upper case (2) and the lower case (1) is provided with chutes (14, 15) which are used to facilitate the upper case (2) and the lower case (1) to depart from and approach to each other vertically, and ends of the rockers (7, 8) fit with the chutes (14, 15).

10 Claims, 2 Drawing Sheets

ROCKER-CHUTE TYPE FINGER-CLIPPED OXIMETER

FIELD OF THE INVENTION

The present invention relates to a finger-clipped oximeter, and particularly relates to a rocker-chute type finger-clipped oximeter.

BACKGROUND OF THE INVENTION

Normally, a finger-clipped oximeter according to the prior art includes an upper case, a lower case and a pivot which connects the upper case and the to lower case together, and the upper and lower cases apply a clamping pressure to a nail portion of a measured finger through a coil spring. Therefore, the upper case and the lower case can be rotated relatively around the pivot and be separated from each other by a distance.

However, the coil spring which controls the upper- and lower cases is not assembled easily, and is apt to undergo fatigue fracture so that a useful life of the finger-clipped oximeter is reduced.

Additionally, the upper case is connected to the lower case through the structures of the pivot and the coil spring. This kind of connection is neither firm nor reliable. If such finger-clipped oximeter falls off inadvertently, the upper and lower cases may be separated or disengaged from each other.

Furthermore, the upper case is connected to the lower case through the structures of the pivot and the coil spring so that the upper and lower cases move in the directions which are not parallel to each other, thereby, offering a poor comfort to a user in measurement.

SUMMARY OF THE INVENTION

An object of the present invention is to provide a finger-clipped oximeter which is assembled easily and operates stably.

Another object of the present invention is to provide a finger-clipped oximeter, a useful life of which can be improved.

Still another object of the present invention is to provide a finger-clipped oximeter, the connection in which is firm and reliable, and the upper and lower cases of which may not be separated or disengaged from each other when the finger-clipped oximeter falls off inadvertently.

Yet still another object of the present invention is to provide a finger-clipped oximeter, when a finger is inserted between the upper and lower cases of the finger-clipped oximeter to be measured, the upper and lower cases can always contact with the finger, which can improve comfort of the user in measurement.

For this reason, the present invention provides a finger-clipped oximeter comprising an upper case and a lower case, characterized in that one of the upper case and the lower case is provided with a guide post which enables the upper case and the lower case to depart from and approach to each other vertically, the other of the upper case and the lower case is provided with a guide sleeve which enables the upper case and the lower case to depart from and approach to each other vertically, and a return spring is provided between an end of the guide post and the case provided with the guide sleeve; and one of the upper case and the lower case is provided with rockers which are used to facilitate the upper case and the lower case to depart from and approach to each other vertically, the other of the upper case and the lower case is provided with chutes which are used to facilitate the upper case and the lower case to depart from and approach to each other vertically, and ends of the rockers fit with the chutes.

Preferably, the upper case is provided with the guide post which enables the upper case and the lower case to depart from and approach to each other vertically; the lower case is provided with the guide sleeve which enables the upper case and the lower case to depart from and approach to each other vertically; and the return spring is a cantilevered plate spring.

Preferably, the lower case is provided with the rockers which are used to facilitate the upper case and the lower case to depart from and approach to each other vertically; and the upper case is provided with the chutes which are used to facilitate the upper case and the lower case to depart from and approach to each other vertically.

Preferably, the rockers which are provided on the lower case are a U-shaped structure which extends through the lower case; a bottom of the U-shaped structure extends through the lower case along a horizontal direction which extends through the lower case; and two side arms of the U-shaped structure are kept parallel to longitudinal side surfaces of the lower case.

Preferably, the two side arms of the U-shaped structure are provided with ends which are bent toward the center of the U-shaped structure respectively; the chutes which are provided on the upper case face both outer sides of the upper case; and the ends of the two side arms of the U-shaped structure fit with the chutes of the upper case respectively.

Preferably, two sets of the same rockers are provided along a longitudinal direction of the lower case, and two sets of the same chutes are provided along a longitudinal direction of the upper case.

Preferably, the chutes of the upper case are provided along a horizontal direction of the upper case.

Preferably, the chutes of the upper case are inclined at an angle of ±20° with respect to the horizontal direction of the upper case.

Preferably, a gap in a range of 0.2-0.8 mm is provided between the guide post and the guide sleeve.

Preferably, dependent on an inclination angle of the chutes with respect to the horizontal direction of the upper case, lengths of the rockers are in a range of 16-20 mm.

According to the present invention, the structure of the coil spring in the prior art is canceled so that the finger-clipped oximeter is assembled easily.

According to the present invention, the structure of the coil spring in the prior art is replaced with a structure of the plate spring so that the useful life of the finger-clipped oximeter can be prolonged.

According to the present invention, the upper case and the lower case of the finger-clipped oximeter are connected with each other through a guide post-guide sleeve structure, which ensures a firm and reliable connection, and the upper case and the lower case will not be separated or disengaged from each other when the finger-clipped oximeter falls off inadvertently.

According to the present invention, a certain gap is provided between the guide post and the guide sleeve provided on the upper case and the lower case of the finger-clipped oximeter, thus not only the operation is caused to be easy and flexible, but also a certain angle is opened between the upper case and the lower case to accommodate to the shape of the finger when they rise up or drop down along the guide post and the guide sleeve, so that the finger-clipped oximeter can be used more conveniently and comfortably.

According to the present invention, when the measurement is performed, the upper case and the lower case can apply an appropriate clamping force to the finger utilizing a return spring, such as the plate spring, to ensure effectiveness and accuracy of the measurement.

According to the present invention, the upper case and the lower case are directed by the guide post-guide sleeve structure, and a mechanism of the rocker and the chute which are coaxial in a left-right direction causes the upper and lower cases to be always kept in such a posture as to contact with the finger when an angle is opened between the upper and lower cases and the upper and lower cases rise up and drop down. When the finger is inserted between the upper case and the lower case to be measured, a deadlock phenomenon of the conventional oximeter caused by nonparallel movements in the horizontal direction can be eliminated, and the comfort of a user in measurement is improved.

DETAILED DESCRIPTION OF THE PREFERRED EMBODIMENTS

Figure 1:
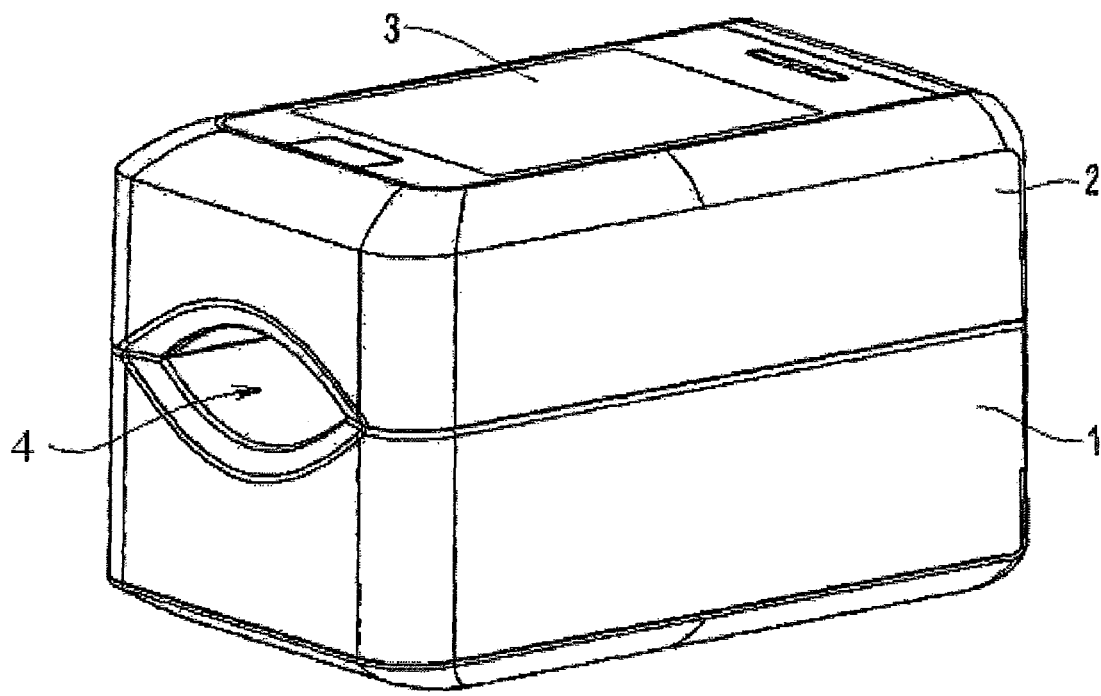
FIG. 1 is a perspective view of a finger-clipped oximeter according to the present invention which in a non-working state.

According to an embodiment of the present invention, as shown in FIG. 1, a finger-clipped oximeter includes a lower case 1, an upper case 2, a display 3 and a finger inserting hole 4.

Figure 2:
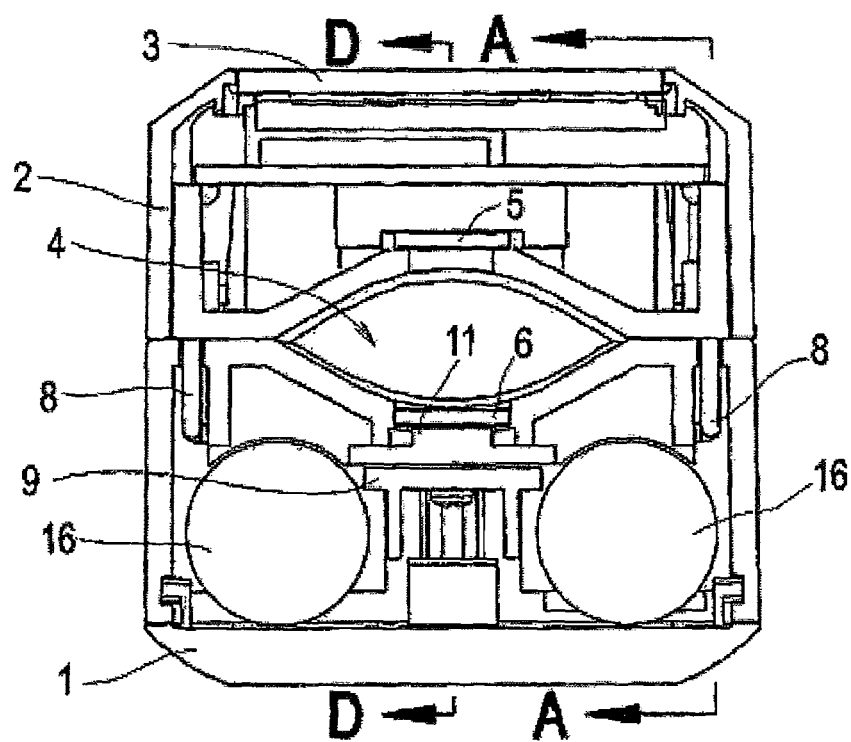
FIG. 2 is a transversal section view of the finger-clipped oximeter shown in FIG. 1 taken along a longitudinal central portion thereof.

In this embodiment, as shown in FIG. 2, a measuring element 5 is provided in the upper case 2, and a measuring element 6 is provided in the lower case 1. Batteries 16 are also provided in the lower case 1. Arm portions on both sides of a rocker 8 can be seen in FIG. 2.

Figure 3:
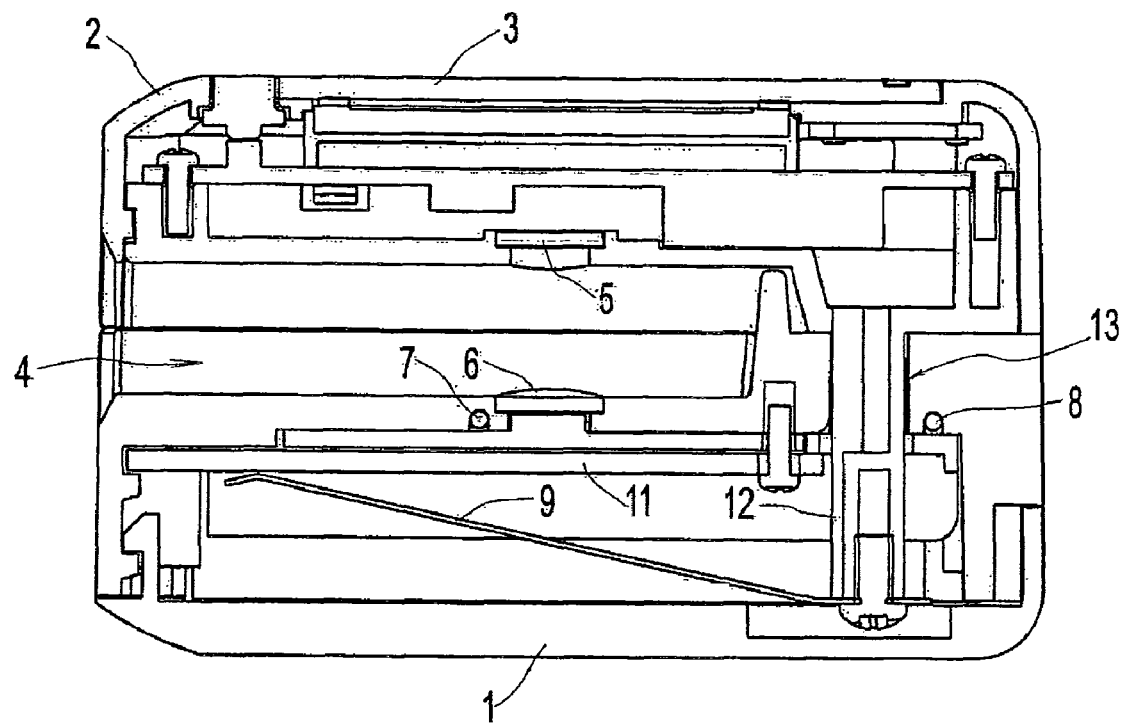
FIG. 3 is a longitudinal section view taken along a line D-D in FIG. 2.

As shown in FIG. 3, a guide post 12 is provided in the upper case 2, and a guide sleeve 13 is provided in the lower case 1. A rocker 7 and the rocker 8 are also provided in the lower case 1. A central horizontal portion of the rocker 8 which passes through the lower case 1 can be seen in FIG. 3. A cantilevered plate spring 9 is provided at an end of the guide post 12, and a free end of the plate spring 9 abuts against an action plate 11 within the lower case 1.

The cantilevered plate spring 9 and the action plate 11 can also be seen in FIG. 2.

When the upper case 2 is caused to move upward with respect to the lower case 1 and it is ready for a finger to insert into the opened finger inserting hole 4, the guide post 12 in the upper case 2 slides upward with respect to the guide sleeve 13 in the lower case 1, and the free end of the cantilevered plate spring 9 which is mounted at the end of the guide post 12 is pushed downward by the action plate 11 in the lower case 1 so that restoring energy is accumulated in the cantilevered plate spring 9.

When the measurement is completed and the finger is pulled out of the finger inserting hole 4, the free end of the cantilevered plate spring 9 which is mounted at the end of the guide post 12 applies a upward pushing force to the action plate 11 in the lower case 1 so that the guide sleeve 13 in the lower case 1 slides upward with respect to the guide post 12 in the upper case 2, thus the upper case 2 is closed with respect to the lower case 1.

Figure 4:
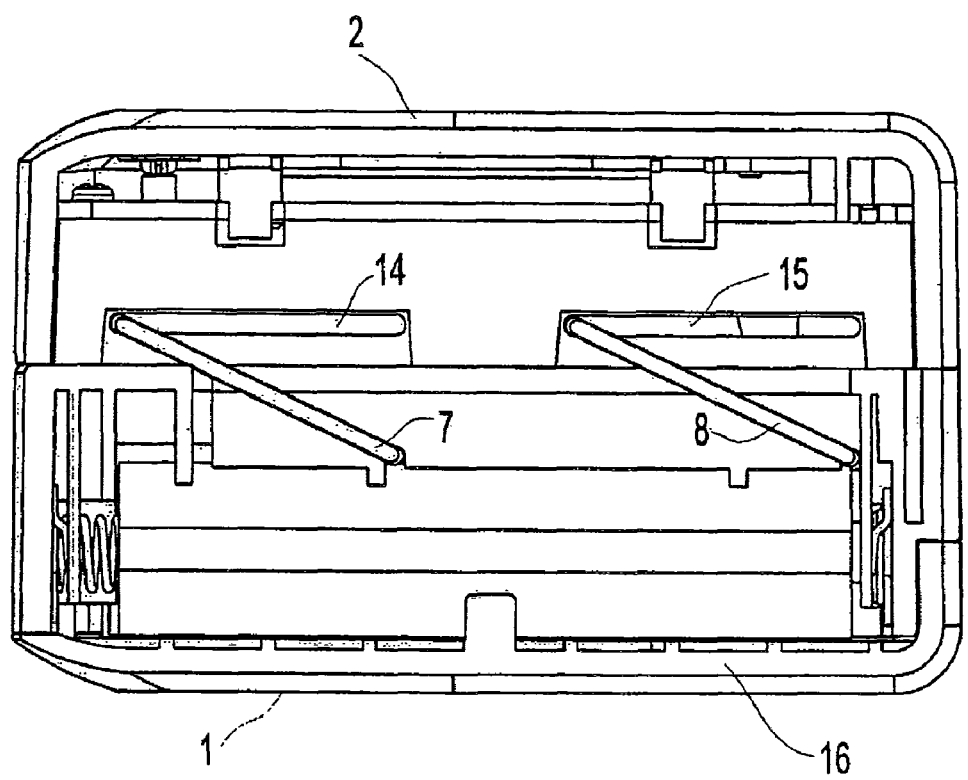
FIG. 4 is a longitudinal section view taken along a line A-A in FIG. 2.

As shown in FIG. 4, the rockers 7 and 8 are provided in the lower case 1, and corresponding chutes 14 and 15 are provided in the upper case 2. Ends of the rockers 7 and 8 fit with the chutes 14 and 15 respectively. Therefore, the ends of the rockers 7 and 8 can slide in the chutes 14 and 15 respectively. In this way, the upper case 2 and the lower case 1 can move in an up-down direction under the action of the guide post 12 and the guide sleeve 13 so that the upper case 2 can always be aligned with the lower case 1 in the up-down direction, thereby ensuring that the measuring elements 5 and 6 can be aligned with each other in the up-down direction, and then ensuring effectiveness and accuracy of the measurement.

Under the action of the guide post 12 and the guide sleeve 13, the upper case 2 and the lower case 1 can cause a clamping force to be distributed on the clamped portion of the finger uniformly.

A certain gap may be provided between the guide post 12 and the guide sleeve 13, for example, a gap of 0.2-0.8 mm, preferably 0.3-0.5 mm, and more preferably 0.4 mm is provided between the guide post 12 and the guide sleeve 13. As a result, the upper case 2 and the lower case 1 can be slightly inclined with respect to each other so as to accommodate to the shape of the finger, thus the user will feel more comfort with the finger.

According to the embodiment of the present invention, as shown in FIGS. 1 to 4, the upper case 2 is provided with the guide post 12 which enables the upper case 2 and the lower case 1 to depart from and approach to each other vertically, and the lower case 1 is provided with the guide sleeve 13 which enables the upper case 2 and the lower case 1 to depart from and approach to each other vertically. The return spring is the cantilevered plate spring 9.

In this embodiment, the rockers 7 and 8 which are used to facilitate the upper case 2 and the lower case 1 to depart from and approach to each other vertically are provided in the lower case 1, and the chutes 14 and 15 which are used to facilitate the upper case 2 and the lower case 1 to depart from and approach to each other vertically are provided in the upper case 2.

In this embodiment, the rockers 7 and 8 which are provided in the lower case 1 are the U-shaped structure which extends through the lower case 1, and the bottom of the U-shaped structure extends through the lower case 1 along a horizontal direction which extends through the lower case 1 (see FIG. 3). Two side arms of the U-shaped structure are kept parallel to longitudinal side surfaces of the lower case 1 (see FIG. 2).

The two side arms of the U-shaped structure are provided with ends which are bent toward the center of the U-shaped structure respectively (not shown). The chutes 14 and 15 which are provided in the upper case 2 face both outer sides of the upper case 2 (FIG. 4). The ends of the two side arms of the U-shaped structure fit with the chutes 14 and 15 of the upper case 2 respectively.

As shown in FIG. 4, two sets of the same rockers 7 and 8 are provided along a longitudinal direction of the lower case 1, and two sets of the same chutes 14 and 15 are provided along a longitudinal direction of the upper case 2. The chutes 14 and 15 of the upper case 2 are provided in a horizontal direction of the upper case 2.

In order to make the operation flexible and convenient, a gap of 0.3-0.5 mm, preferably 0.4 mm can be provided between the guide post 12 and the guide sleeve 13.

In other embodiments according to the present invention, the guide post may be provided in the lower case, and the guide sleeve may be provided in the upper case. As for the return spring, a screw spring or a pair of magnets which have a mutual repelling force, and the like, may be used. The chutes may be provided in the lower case, and the rockers may be provided in the upper case.

In addition, the chutes may be inclined by a certain angle with respect to a horizontal direction of a case to facilitate the relative movement between the upper case and the lower case in a labor-saving manner. In one embodiment, the chutes are inclined at an angle of ±20° with respect to the horizontal direction of the upper case, thus not only it is easy for the upper case to rise up or drop down, but also the finger-clipped oximeter has a compact structure.

Specially, an optimal length of the rockers can be determined based on an inclination angle of the chutes with respect to the horizontal direction of the upper case. In another embodiment, the lengths of the rockers are generally in a range of 16-20 mm.

As described above, it can be understood that the finger-clipped oximeter according to the present invention includes the upper case 2 and the lower case 1, wherein one of the upper case 2 and the lower case 1 is provided with the guide post 12 which enables the upper case 2 and the lower case 1 to depart from and approach to each other vertically, the other of the upper case 2 and the lower case 1 is provided with the guide sleeve 13 which enables the upper case 2 and the lower case 1 to depart from and approach to each other vertically, and the return spring 9 is provided between the end of the guide post 12 and the case provided with the guide sleeve 13; and wherein one of the upper case 2 and the lower case 1 is provided with the rockers 7 and 8 which are used to facilitate the upper case 2 and the lower case 1 to depart from and approach to each other vertically, the other of the upper case 2 and the lower case 1 is provided with the chutes 14 and 15 which are used to facilitate the upper case 2 and the lower case 1 to depart from and approach to each other vertically, and the ends of the rockers 7 and 8 fit with the chutes 14 and 15.

Although several embodiments of the present invention have been disclosed, various modifications, improvements and substitutions can be made to the present invention, as understood by those skilled in the art, however, all of the modifications, improvements and substitutions will fall within the scope of the invention defined by the appended claims.

What is claimed is:

1. A finger-clipped oximeter comprising an upper case and a lower case, characterized in that
   one of the upper case and the lower case is provided with a guide post which enables the upper case and the lower case to depart from and approach to each other vertically, the other of the upper case and the lower case is provided with a guide sleeve which enables the upper case and the lower case to depart from and approach to each other vertically, and a return spring is provided between an end of the guide post and the case provided with the guide sleeve; and
   one of the upper case and the lower case is provided with rockers which are used to facilitate the upper case and the lower case to depart from and approach to each other vertically, the other of the upper case and the lower case is provided with chutes which are used to facilitate the upper case and the lower case to depart from and approach to each other vertically, and ends of the rockers fit with the chutes.

2. The finger-clipped oximeter according to claim 1, characterized in that
   the upper case is provided with the guide post which enables the upper case and the lower case to depart from and approach to each other vertically;
   the lower case is provided with the guide sleeve which enables the upper case and the lower case to depart from and approach to each other vertically; and
   the return spring is a cantilevered plate spring.

3. The finger-clipped oximeter according to claim 1, characterized in that
   the lower case is provided with rockers which are used to facilitate the upper case and the lower case to depart from and approach to each other vertically; and
   the upper case is provided with chutes which are used to facilitate the upper case and the lower case to depart from and approach to each other vertically.

4. The finger-clipped oximeter according to claim 3, characterized in that
   the rockers which are provided in the lower case are a U-shaped structure which extends through the lower case;
   a bottom of the U-shaped structure extends through the lower case along a horizontal direction which extends through the lower case; and two side arms of the U-shaped structure are kept parallel to longitudinal side surfaces of the lower case.

5. The finger-clipped oximeter according to claim 4, characterized in that
   two side arms of the U-shaped structure are provided with ends which are bent toward the center of the U-shaped structure respectively;
   the chutes which are provided in the upper case face both outer sides of the upper case; and
   the ends of the two side arms of the U-shaped structure fit with the chutes of the upper case respectively.

6. The finger-clipped oximeter according to claim 1, characterized in that
   two sets of the same rockers are provided along a longitudinal direction of the lower case, and two sets of the same chutes are provided along a longitudinal direction of the upper case.

7. The finger-clipped oximeter according to claim 1, characterized in that
   the chutes of the upper case are provided along a horizontal direction of the upper case.

8. The finger-clipped oximeter according to claim 1, characterized in that
   the chutes of the upper case are inclined at an angle of ±20° with respect to the horizontal direction of the upper case.

9. The finger-clipped oximeter according to claim 8, characterized in that
   based on an inclination angle of the chutes with respect to the horizontal direction of the upper case, lengths of the rockers are in a range of 16-20 mm.

10. The finger-clipped oximeter according to claim 1, characterized in that
    a gap of 0.2-0.8 mm is provided between the guide post and the guide sleeve.

* * * * *